United States Patent [19]
Yoshikumi et al.

[11] Patent Number: 4,632,743
[45] Date of Patent: Dec. 30, 1986

[54] METHOD FOR EXAMINING CELLS BY ELECTROPHORESIS

[75] Inventors: Chikao Yoshikumi, Kunitachi; Kenichi Matsunaga, Tokyo; Haruhisa Hayashi, Tokyo; Yoshiharu Oguchi, Tokyo, all of Japan

[73] Assignee: Kureha Kagaku Kogyo Kabushiki Kaisha, Tokyo, Japan

[21] Appl. No.: 568,951

[22] Filed: Apr. 25, 1984

Related U.S. Application Data

[63] Continuation-in-part of Ser. No. 389,549, Jun. 17, 1982, abandoned.

[30] Foreign Application Priority Data

Jul. 9, 1981 [JP] Japan ................................ 56-107399

[51] Int. Cl.[4] ............................................. G01N 27/26
[52] U.S. Cl. ............................... 204/183.3; 204/182.7; 204/182.8
[58] Field of Search ........... 204/180 R, 180 G, 180 S, 204/183.3, 182.7, 182.8

[56] References Cited

U.S. PATENT DOCUMENTS

| | | | |
|---|---|---|---|
| 3,140,714 | 7/1964 | Murphy et al. | 204/180 R |
| 3,984,533 | 10/1976 | Uzgiris | 204/180 R |
| 3,988,230 | 10/1976 | Krotz | 204/180 S |
| 4,061,561 | 12/1977 | Fletcher et al. | 204/180 G |
| 4,198,389 | 4/1980 | Wadsworth | 204/180 G |
| 4,212,650 | 7/1980 | Bauer et al. | 204/180 R |
| 4,225,405 | 9/1980 | Lawson | 204/180 R |
| 4,239,612 | 12/1980 | Goetz | 204/180 R |
| 4,268,268 | 5/1981 | Blum | 204/180 G |
| 4,326,934 | 4/1982 | Pohl | 204/180 R |
| 4,332,472 | 6/1982 | Kato | 204/180 S |

FOREIGN PATENT DOCUMENTS 2054839  2/1981  United Kingdom ........... 204/180 R

OTHER PUBLICATIONS

Abramson et al., The Electro Chemical Society Preprint, 71-12 (1937 meeting), pp. 115-131.
Zwergel et al., Microscopia Acta 80(1978) pp. 383-390.
Kyorin Abstract of Japanese Patent 56-1351.

*Primary Examiner*—John F. Niebling
*Assistant Examiner*—B. J. Boggs, Jr.
*Attorney, Agent, or Firm*—Wegner & Bretschneider

[57] ABSTRACT

Cells, particularly lymphocytes in peripheral blood or lymphatic tissues such as thymus, spleen and lymph node, are examined by measuring an electrophoretic property, such as a fraction of the number of the cells having an electrophoretic mobility within a predetermined range to the total number of the cells to be examined, with the aid of an automatic electrophoretic apparatus which is operated in a medium of the physiological conditions and by reversing the electric field, and comparing the obtained pattern of the electrophoretic property of the cells to be examined with the pattern of the electrophoretic property of normal host-cells, in order to diagnose cancer.

10 Claims, 11 Drawing Figures in
METHOD FOR EXAMINING CELLS BY ELECTROPHORESIS This application is a continuation-in-part application of U.S. application Ser. No. 389,549, filed June 17, 1982, now abandoned.

BACKGROUND OF THE INVENTION

This invention relates to a method for examining cells, particularly, lymphocytes, leukocytes or the like by electrophoresis.

In recent years, cell electrophoresis has begun to attract attention as a means for examining cellular immunity. One of the methods of cell electrophoresis was proposed by D. Sabolovic et al., "Cell Electrophoresis: Clinical Application and Methodology", INSERM Symposium No. 11 (1979). In this method, it necessarily takes a long time due to manual operation to obtain results, and the method is not favorable for examining a number of living cells. As another method, a laser-Doppler method was developed by D. Steiner et al., European Journal of Cancer, 15, 1275-1280 (1979), however, no satisfactorily good resolution of an electrophoretic pattern is obtained.

In these situations, a development of an apparatus and a method of electrophoresis of high performance enabling the rapid determination has been desired.

It is an object of the invention to provide a method for examining cells, particularly lymphocytes in peripheral blood or lymphatic tissues, comprising measuring an electrophoretic property of cells by an automatic electrophoretic apparatus and comparing the obtained pattern of the electrophoretic property of cells to be examined with the pattern of the electrophoretic property of normal host-cells.

DETAILED DESCRIPTION OF THE INVENTION high resolved pattern, the informations which have never been obtained can be available from the change of electrophoretic pattern.

The automatic electrophoretic apparatus used in the invention has the characteristic features as follows:

(1) it can afford to examine a large number of cells in a short period of time, (2) since the average electrophoretic mobility of individual cell can be determined by reversing the electric field, the accuracy of measured values is high, (3) platelets, minute suspended substances such as intermingled substances, agglomerated cells do not measured, and (4) a medium in the physiological conditions (for instance, the ionic strength, I, being 0.15) can be used as a liquid suspension of cells to be electrophoretically examined.

Particularly concerning the feature (4), there have been hitherto many reports on the determination under the different conditions (for instance, I being 0.005 to 0.1) from the physiological condition because of the limitation of the apparatus and the measurement, however, it is preferable to use a liquid suspension of cells in the physiological conditions from the viewpoint of examining the living cells.

In addition, an automatic microscopic apparatus for electrophoresis (Parmoquant-II, made by Karl-Zeiss Co., Deutsche Demokratische Republik, hereinafter abbreviated as PQ-II) used in Examples below may be operated so as to measure exactly the average electrophoretic mobility of each cell among a large number of cells by reversing the electric field and whereby a histogram of the mobility may be obtained. In the course of operation, the concentration of the cells in the specimen (aqueous suspension of the cells) is adjusted to 0.5 to $20 \times 10^6$ cells/ml, and the ionic strength of the aqueous suspension of the cells is adjusted to 0.11 to 0.21, preferably, 0.13 to 0.017.

However, any other apparatus can be used in the invention, for instance, a laser-Doppler type, a lasergrating type, a free-flowing type and the like, so far as fulfilling the above-mentioned conditions (1) to (4).

The method of the invention while using the apparatus PQ-II will be described in detail, for example, in the examination of thymocytes of a normal C3H/He mouse and a tumor (X-5563) bearing C3H/He mouse.

Figure 1:
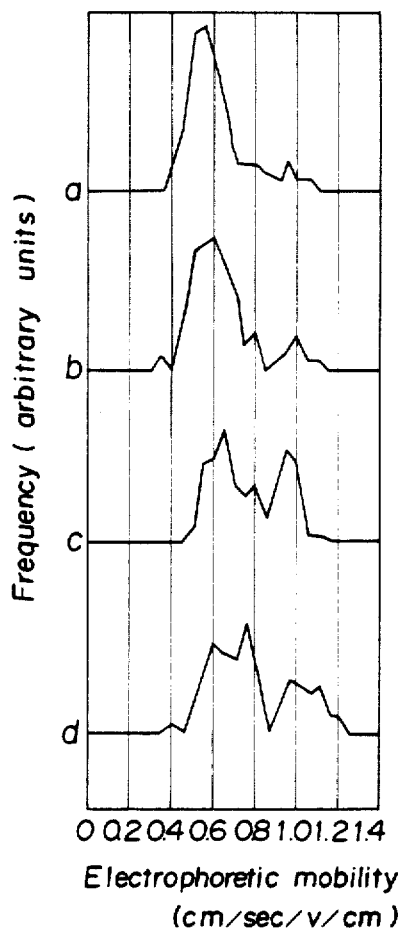
FIG. 1 is a diagramatic representation of comparative patterns of electrophoretic mobilities between the thymocytes of a normal C3H/He mouse (a) and tumor (X-5563) bearing mice at 5 day intervals after transplantation, (b) (c) and (d) respectively.

The patterns of electrophoretic mobilities obtained are shown in FIG. 1, a normal mouse (a), a mouse after 5 days (b), 10 days (c) and 15 days (d) of the transplantation, respectively, while taking the electrophoretic mobility (cm/sec/V/cm) in the abscissa and the frequency (arbitrary units) in the ordinate.

As seen in FIG. 1, the main peak of the pattern began to show a deformation after 5 days of the transplantation, and the patterns after 10 days and 15 days of the transplantation were quite different from that of the lymphocytes of the normal mouse.

For evaluating by numerical values the electrophoretic pattern, a mean value of mobilities, a mobility of main peak, an average mobility of cells showing a mobility within a predetermined range and a fraction of the number of cells showing a mobility within a predetermined range to the total number of the cells may be used.

For instance, in FIG. 1 (a) the number of cells having a higher mobility than 0.70 cm/sec/V/cm which is the boundary of the larger peak and the smaller peak was 20.5% of the total number of the cells, while in FIG. 1, (b), (c) and (d) the numbers of the cells having a higher mobility than 0.70 cm/sec/V/cm were 24.2, 51.9 and 68.4%, respectively. In other words, as the time passes after the transplantation of tumor cells, the fraction of the number of cells having a higher mobility than 0.70 cm/sec/V/cm to the total number of the cells becomes larger by about 4–48% than the corresponding fraction of the normal mouse. The mobility of the boundary between the larger peak and the smaller peak in the electrophoretic pattern of lymphocytes, and the fraction of the number of the cells having a higher mobility than the boundary mobility to the total number of the cells in a normal animal are a little affected by the species, the strains and the number of days after birth of the animal.

The average mobilities of the larger peak and the smaller peak in the electrophoretic pattern of the lymphocytes of the normal mouse shown in FIG. 1, (a) were 0.52 and 0.95 cm/sec/V/cm, respectively. Similarly, those of the lymphocytes of the mouse after 5, 10 and 15 days of the transplantation were 0.58 and 0.97 in (b), 0.62 and 0.98 in (c) and 0.68 and 1.03 in (d), respectively.

Thus, the average mobilities of both the larger peak and the smaller peak in the electrophoretic patterns of the mouse after transplantation of tumor cells shifted towards higher mobilities.

Figure 2:
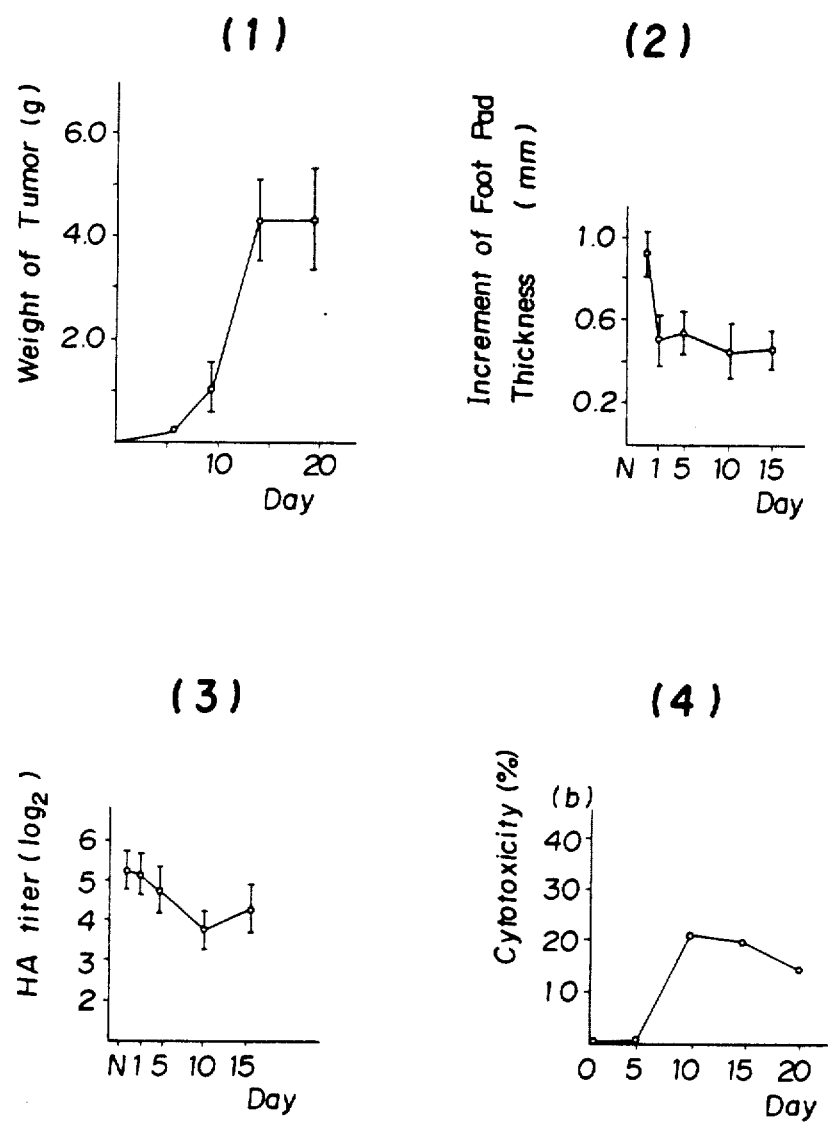
FIG. 2 presents data from 4 conventional methods of determining cancer showing that abnormal values appear from the 5th to 10th day after transplantation of tumor tissue: (1) graphically depicts weight changes in tumors (2) graphically shows increments of foot pad thicknesses (3) graphically presents the production of antibody against sheep erythrocytes (4) graphically demonstrates changes in in vitro cytotoxic activity of lymphocytes against the tumor.

In order to compare the method of the invention with the conventional method, the results of determination of the weight of tumor, the delayed foot pad reaction against sheep erythrocytes, the productivity of antibody against sheep erythrocytes and the in vitro cytotoxic activity of lymphocytes against the tumor are shown in FIG. 2, (1) to (4). In FIG. 2, the days after tumor inoculation is taken in the abscissa and the weight of tumor, the increment of the foot pad thickness, the value of productivity of antibody (titer) and the cytotoxic activity of lymphocytes are taken in the ordinate of FIG. 2, (1), (2), (3) and (4), respectively. As seen from FIG. 2, the abnormal values appear from 5th to 10th day corresponding to the appearance of the change in electrophoretic pattern.

These facts have been recognized in various experimental animal species, and the number of lymphocytes of a higher electrophoretic mobility in the tumor-bearing host increased by 4–70% as compared with that of the normal animal.

When the fraction of the number of cells having a higher mobility to the total number of the cells in the tumor-bearing host is divided by the corresponding fraction of the normal host-cells, the ratio falls within the range of 1.05 to 8.00. Further, the ratio of the average mobility of a peak in the tumor-bearing host to the corresponding mobility of the normal host-cells is in the range of 1.02 to 1.60.

The results obtained by the method of examination of the invention correspond to the results of determination of immunity by the conventional method, and the method for examining cells of the invention is a superior and quicker method than the conventional method.

On the contrary, in the case of the electrophoretic pattern of peripheral lymphocytes the number of lymphocytes of the lower electrophoretic mobility in tumor-bearing host increases by 4–70% as compared with that of normal host as shown in Examples below.

When the fraction of the number of cells having a higher mobility to the total number of the cells in the tumor-bearing host is divided by the corresponding fraction of the normal host-cells, the ratio falls within the range of 0.30 to 0.95. Further, the ratio of the average mobility of a peak in the tumor-bearing host to the corresponding mobility of the normal host-cells is in the range of 0.60 to 1.00.

The method of the invention is useful in examining immune cells not only of animals but also of human being, particularly in diagnosticating cancer.

The invention will be illustrated more in detail while referring to the following non-limitative examples.

EXAMPLE 1

After transplanting $1 \times 10^6$ cells of Sarcoma-180 to the left axillary site of a female ICR mouse of 8 weeks after birth, the mouse was sacrificed at the 25th day to extirpate the thymic cells, and the cells were isolated by a pincette and passed through a mesh to be isolated. After subjecting the isolated cells to hypotonic treatment for removing erythrocytes and washing the thus treated cells two times with Eagle's MEM (minimum essential medium), the cells were suspended in Eagle's MEM at a concentration of $10^6$ to $10^7$ cells/ml.

Before extirpating the thymus, peripheral blood specimen was collected from the mouse, while using an injector with its wall surface moisted with a solution containing 2.5 units (per ml of blood specimen) of sodium heparinate, and after diluting the blood specimen with the same volume of Hanks' balanced salt solution (hereinafter abbreviated as HBSS) and mixing thoroughly, the diluted specimen was placed while forming a layer of about 5 ml on 3 ml of Ficoll-Paque solution (Grade: Ficoll 400, made by Pharmacia Fine Chemical Co., a mixed solution of sodium diatriazoate; specific gravity of 1.077) in a test tube without disturbing the interface between the two solutions. Then the content of the test tube was subjected to centrifugation for 30 min at 400 G, and the lymphocytes in the interface of the diluted specimen and the Ficoll-Paque solution were collected by a Pasteur-pepette.

The thus collected lymphocytes were washed two times with HBSS centifugally each time for 10 min at 260 G, and then further washed centrifugally with Eagle's MEM for 10 min at 180 G. After discarding the supernatant solution, the remaining lymphocytes were dispersed in Eagle's MEM at a concentration of the cells of 5 to $10 \times 10^6$ cells/ml.

The thus obtained two ml of specimen suspended in Eagle's MEM were subjected to electrophoretic examination by a method of fully automatic determination in PQ-II under the conditions of dark-field illumination, an object lens of 25 magnifications and electrophoretic current of 10 mA to obtain the results spelled out by a printer as the histogram and the average mobility of the lymphocytes.

According to the same procedures, the thymocytes and the peripheral lymphocytes of normal mouse of the same strain were examined. The histograms a and b in FIG. 3 are the electrophoretic patterns of the thymocytes from the normal mouse and the tumor-bearing mouse, respectively, and those of a and b in FIG. 4 are the electrophoretic patterns of the peripheral lymphocytes from the normal mouse and the tumor-bearing mouse, respectively.

Figure 3:
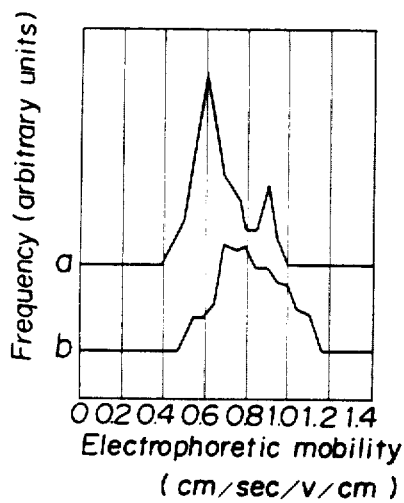
FIG. 3 is a representation of a histogram of the electrophoretic patterns of the thymocytes from a normal mouse (a) and a tumor-bearing mouse (b).

As seen in FIG. 3, a, the electrophoretic pattern of the thymocytes of the normal mouse shows a two-peaked pattern with a larger peak at a mobility of 0.6 cm/sec/V/cm and a smaller peak at a mobility of 0.9 cm/sec/V/cm, while that of the tumor-bearing mouse shows a pattern with a broadened peak of a mobility which shifted toward the higher mobility as seen in FIG. 3, b.

Figure 4:
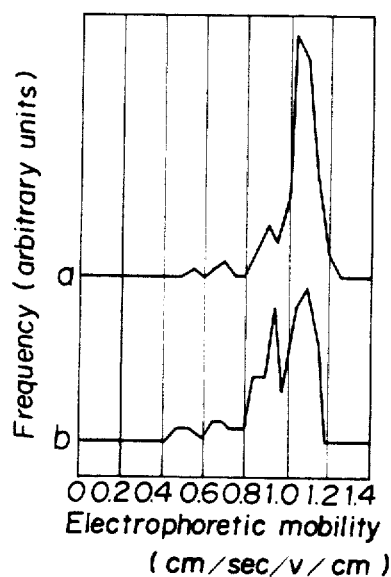
FIG. 4 is a representation of a histogram of the electrophoretic patterns of the peripheral lymphocytes from a normal mouse (a) and a tumor bearing mouse (b).

Also, the electrophoretic pattern of the peripheral lymphocytes of the tumor-bearing mouse (in FIG. 4, b) shows a broader peak pattern and the fraction of the number of lymphocytes with lower mobility to the total number of lymphocytes increases as compared to those of the normal mouse (in FIG. 4, a).

EXAMPLE 2

Figure 5:
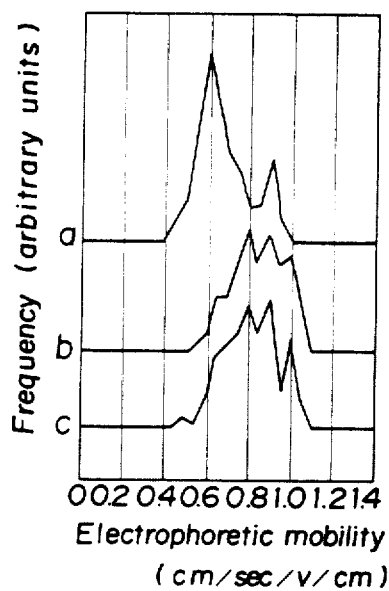
FIG. 5 is a representation of a histogram of the electrophoretic patterns of the thymocytes of a normal mouse (a) and tumor bearing mice (b: Sarcoma 1800°; c.: Ehrlich's tumor).

After 8 days of transplanting $5 \times 10^6$ cells of Sarcoma-180 or Ehrlich's tumor to a female ICR mouse of 8 weeks after birth intraperitoneally, the thymocytes were collected from the mouse in the same procedures as in Example 1, and subjected to the electrophoretic examination under the same conditions as in Example 1 to obtain the results shown in FIG. 5, b (Sarcoma-180) and c (Ehrlich's tumor) with the result obtained from the normal mouse shown in FIG. 5, a.

As seen in FIG. 5, the electrophoretic patterns of the thymocytes of tumor-bearing animal (b and c in FIG. 5) show respectively, a broad peak and the fraction of the number of lymphocytes with a higher mobility to the total number of lymphocytes increases as compared to the patterns of that of the normal mouse.

EXAMPLE 3

Figure 6:
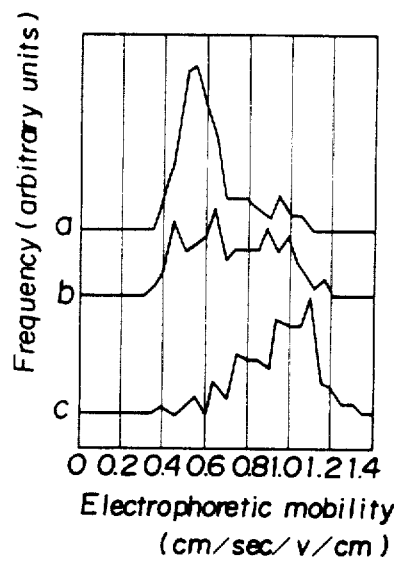
FIG. 6 is a representation of a histogram of the electrophoretic patterns of thymocytes of mice MH-134 tumor cells (h); MM-102 tumor cells (c); and a normal mouse (a).
Figure 7:
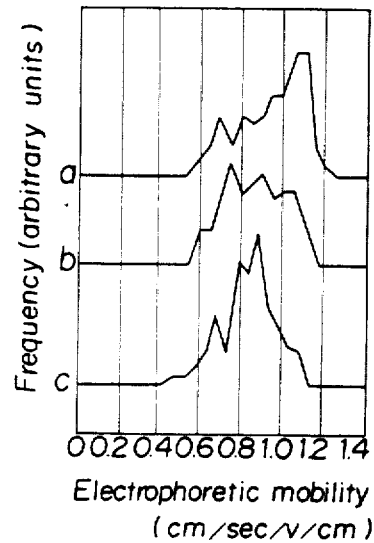
FIG. 7 is a representation of a histogram of the electrophoretic patterns of peripheral lymphocytes of mice MH-134 tumor cells (b); MM-102 tumor cells (c); and a normal mouse (a).

After intraperitoneally transplanting $1 \times 10^6$ cells of MH-134 tumor or MM-102 tumor to a male C3H/He mouse in its 8th week after birth, the thymocytes and the peripheral lymphocyte were collected from the mouse (on the sixth day of transplantation of MH-134 tumor cells, and on the eighth day of MM-102 tumor cells) as in Example 1, and subjected to the electrophoretic examination as in Example 1 to obtain the results shown in FIGS. 6 and 7 wherein the electrophoretic patterns a, b and c are those, respectively, of the normal mouse, mouse with MH-134 tumor and mouse with MM-102.

As seen from the patterns, the tendency of alterations appearing in the patterns of tumor-bearing mice as compared to the pattern of the normal mouse was the same as in Example 1.

EXAMPLE 4

Figure 9:
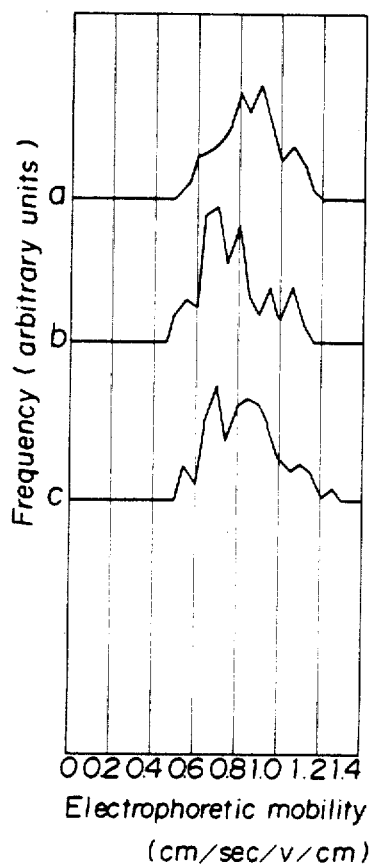
FIG. 9 is a representation of a histogram of the electrophoretic patterns of peripheral lymphocytes of a normal mouse (a), a ca-755 tumor-bearing mouse (b) and a B-16 tumor bearing mouse (c).
Figure 8:
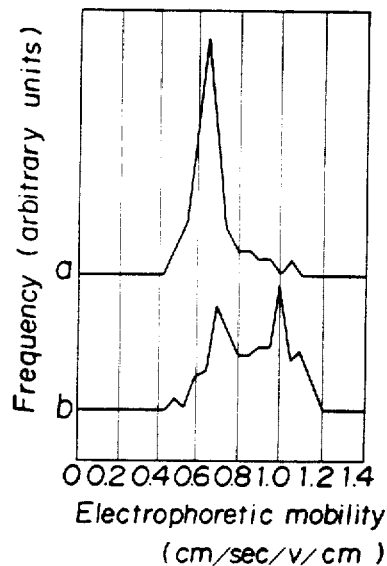
FIG. 8 is a representation of a histogram of the electrophoretic patterns of the thymocytes of a normal mouse (a) and a Lewis lung tumor bearing mouse (b).

After transplanting $1 \times 10^6$ cells of Lewis lung cancer, Ca-755 tumor or B-16 tumor intraperitoneally to a male C57BL/6 mouse in its 8th week after birth, the thymocytes and the peripheral lymphocytes of the mouse were collected on the 9th day and on the 15th day of transplantation, respectively, as in Example 1, and subjected to the electrophoretic examination as in Example 1, the results being shown in FIGS. 8 and 9 together with the results on the same examination on the normal mouse, wherein the pattern a in FIG. 8 is that of the thymocytes of the normal mouse and b in FIG. 8 is those of the Lewis lung tumor-bearing mouse, and the patterns a, b, and c in FIG. 9 are those of the peripheral lymphocytes of the normal mouse, the Ca-755 tumor-bearing mouse and the B-16 tumor-bearing mouse, respectively.

The same tendency was observed in FIGS. 8 and 9 as in Example 1.

EXAMPLE 5

Six specimens of human lymphocytes were prepared from the six peripheral blood specimens taken from a man of age of 35 (a) a man of age of 30 (b), a woman of age of 25 (c), a woman of age of 18 (d), a man of age of 19 (e) and a woman of age of 40 (f), respectively, in the respective injectors containing an aqueous solution containing sodium heparin in an amount of 2.5 unit per ml of the blood, as in Example 1, and after suspending each specimen of the lymphocytes into Eagle's MEM at a concentration of 5 to $10 \times 10^6$ cells/ml, each suspension was examined electrophoretically as in Example 1. The results are shown in FIG. 10 as the six electrophoretic patterns.

Figure 10:
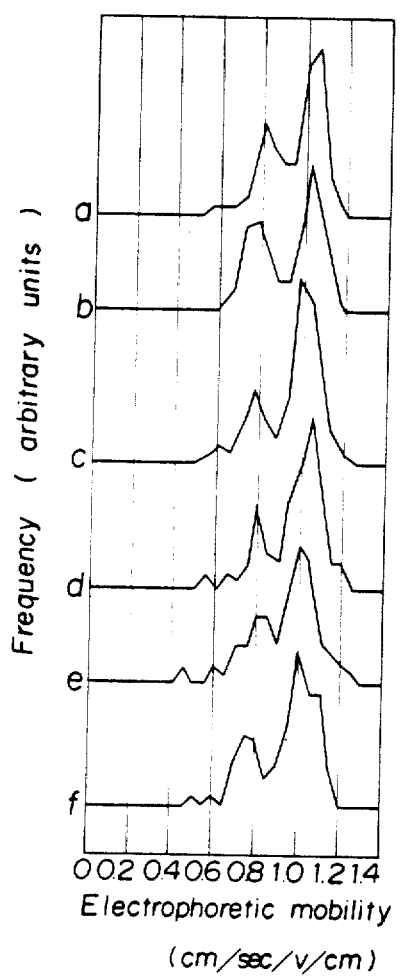
FIG. 10 is a representation of a histogram of the electrophoretic patterns of human lymphocytes prepared from peripheral blood specimens taken from a man of age 35 (a), a man of age 30 (b), a woman of age 25 (c), a woman of age 18 (d), a man of age 19 (e), and a woman of age 40 (f).

As are seen in FIG. 10, all six specimens of human peripheral lymphocytes showed nearly the same electrophoretic patterns comprising the two conspicuous peaks at the respective mobilities of about 0.8 and about 1.0 cm/sec/V/cm.

EXAMPLE 6

Figure 11:
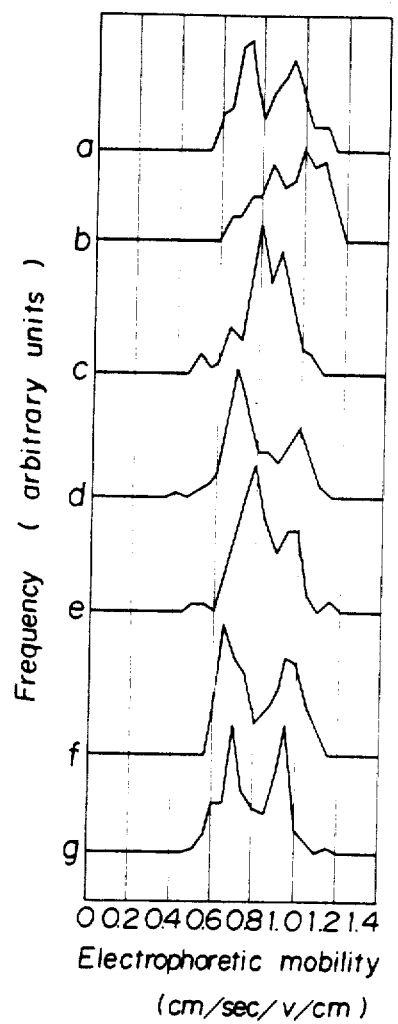
FIG. 11 is a representative of a histogram of the electrophoreitc patterns of the human peripheral lymphocytes taken from a male patient suffering from colon cancer of age 49 (a), male patient suffering from rectal cancer of age 68 (b), a male patient suffering from stomach cancer of age 72 (c), a female patient suffering from breast cancer of age 50 (d), a male patient suffering from recurring esophageal cancer of age 49 (e), a female patient suffering from recurring breast cancer of age 50 (f), and a male patient suffering from recurring pancreatoncus of age 62 (g).

As in Example 5, seven specimens of human peripheral lymphocytes were taken from a male patient of colonal cancer of age of 49 (a), a male patient of rectal cancer of age of 68 (b), a male patient of stomach cancer of age of 72 (c), a female patient of breast cancer of age of 50 (d), a male patient of recurring esophageal cancer of age of 49 (e), a female patient of recurring breast cancer of age of 50 (f) and a male patient of recurring pancreatoncus of age of 62 (g) as in Example 5, and after suspending in Eagle's MEM, examined electrophoretically as in Example 5. The results are shown in FIG. 11 as the electrophoretic patterns a to g corresponding to the letters of the respective patients.

As are seen in the patterns as compared to the patterns in FIG. 10 obtained from normal persons, the peak of the lymphocytes having lower mobility became higher (showing the increased number of the lymphocytes with the lower mobility) than that of normal persons, and the whole pattern showed some disturbance.

What is claimed is:

1. A diagnostic method for determining an electrophoretic property of lymphocytes comprising
   measuring in an automatic electrophoretic apparatus a predetermined electrophoretic property of untreated lymphocytes taken from the peripheral blood or lymph tissues of humans or animals being diagnosed to obtain a pattern, said peripheral blood or lymph tissues being suspended in a physiological solution having an ionic strength of 0.11 to 0.21 at a concentration of $0.5 \times 10^6$ to $20 \times 10^6$ lymphocytes per ml of said physiological solution, and
   comparing the thus-obtained pattern of the electrophoretic property with a pattern of the same electrophoretic property of corresponding normal lymphocytes.

2. The method of claim 1 wherein the ionic strength is between 0.13 to 0.17.

3. The method of claim 1 wherein a fraction of the number of the lymphocytes having an electrophoretic mobility within a predetermined range to the total number of lymphocytes is measured.

4. The method of claim 1 wherein an average electrophoretic mobility of the lymphocytes having an electrophoretic mobility within a predetermined range is measured.

5. The method of claim 1 wherein electrophoretic mobility of a peak in the pattern is measured.

6. The method of claim 1 wherein the automatic electrophoretic apparatus is operated by reversing the electric field.

7. The method of claim 1 wherein the lymphocytes are from peripheral blood and the increase in the fraction of the number of lymphocytes having an electrophoretic mobility lower than a predetermined value to the total number of lymphocytes is measured.

8. The method of claim 1 wherein the lymph tissue is thymus and the lymphocytes are thymocytes.

9. The method of claim 8 wherein the increase in the fraction of the number of thymocytes having an electrophoretic mobility higher than a predetermined value to the total number of thymocytes is measured.

10. The method of claim 1 for diagnosing cancer.

* * * * *

UNITED STATES PATENT AND TRADEMARK OFFICE
CERTIFICATE OF CORRECTION

PATENT NO. : 4,632,743

DATED : December 30, 1986

INVENTOR(S) : Chikao YOSHIKUMI et al.

It is certified that error appears in the above-identified patent and that said Letters Patent is hereby corrected as shown below:   On the title page Please correct the filing date as follows:

Delete "April 25, 1984" and insert --January 6, 1984--.

Signed and Sealed this

Fifth Day of July, 1988

Attest:

DONALD J. QUIGG

*Attesting Officer*   *Commissioner of Patents and Trademarks*